United States Patent
Johansson et al.

(10) Patent No.: US 7,342,999 B2
(45) Date of Patent: Mar. 11, 2008

(54) METHOD AND APPARATUS FOR GENERATION OF A DIGITAL X-RAY IMAGE OF AN EXAMINATION SUBJECT

(75) Inventors: Katrin Johansson, Värmdö (SE); Thomas Mertelmeier, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/499,276

(22) Filed: Aug. 3, 2006

(65) Prior Publication Data
US 2007/0036272 A1    Feb. 15, 2007

(30) Foreign Application Priority Data
Aug. 3, 2005    (DE) ............ 10 2005 036 514

(51) Int. Cl.
*H05G 1/64* (2006.01)
(52) U.S. Cl. ............ 378/98.12; 378/37; 378/62; 378/108; 378/117
(58) Field of Classification Search .......... 378/37, 378/62, 98.7, 98.8, 98.12, 108–112, 115, 378/117
See application file for complete search history.

(56) References Cited

U.S. PATENT DOCUMENTS

| | | | |
|---|---|---|---|
| 5,485,501 A * | 1/1996 | Aichinger | 378/98.7 |
| 6,487,271 B1 | 11/2002 | Laurent | 378/98.9 |
| 7,103,143 B2 * | 9/2006 | Alving et al. | 378/98.7 |
| 2006/0269041 A1 * | 11/2006 | Mertelmeier | 378/37 |

* cited by examiner

*Primary Examiner*—Jurie Yun
(74) *Attorney, Agent, or Firm*—Schiff Hardin LLP

(57) ABSTRACT

In a method and apparatus for generation of a digital x-ray image of an examination subject with an x-ray tube and a digital x-ray detector, a preliminary total dose required for correct exposure is determined using prior knowledge and a complete pre-image of the examination subject is acquired with a partial dose that is smaller than the preliminary total dose. A remaining dose is determined from the pre-image by image evaluation. A complete following image is acquired with this remaining dose, and the final x-ray image is assembled from the pre-image and the following image.

4 Claims, 1 Drawing Sheet

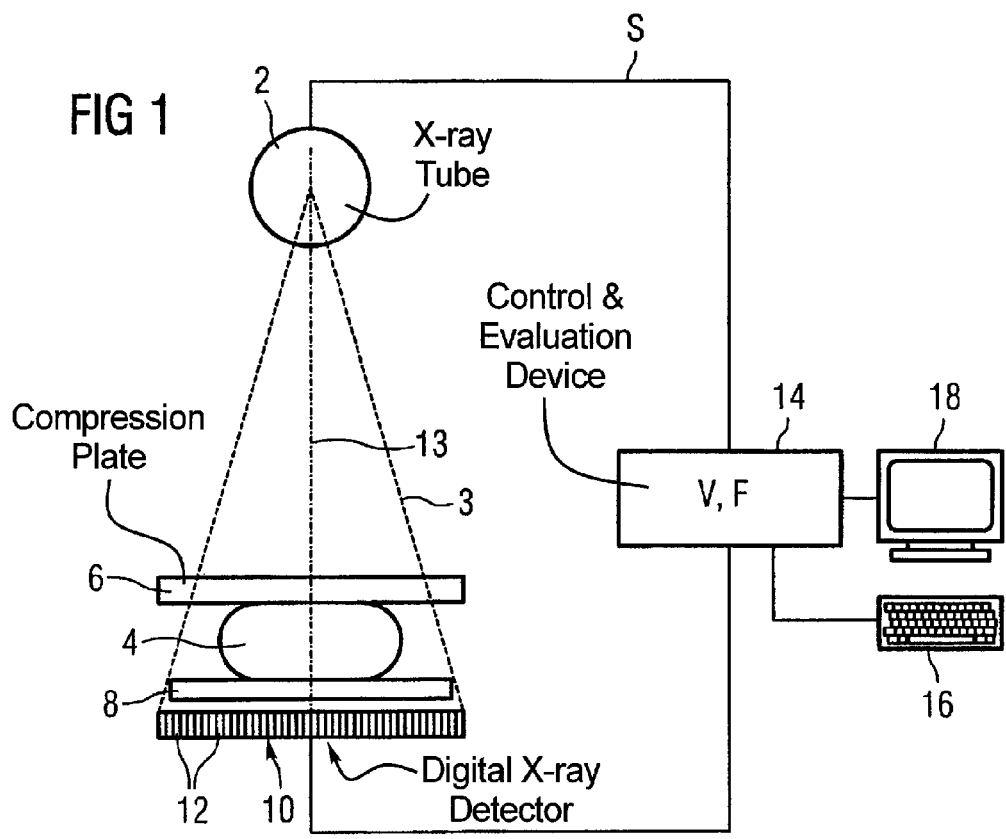
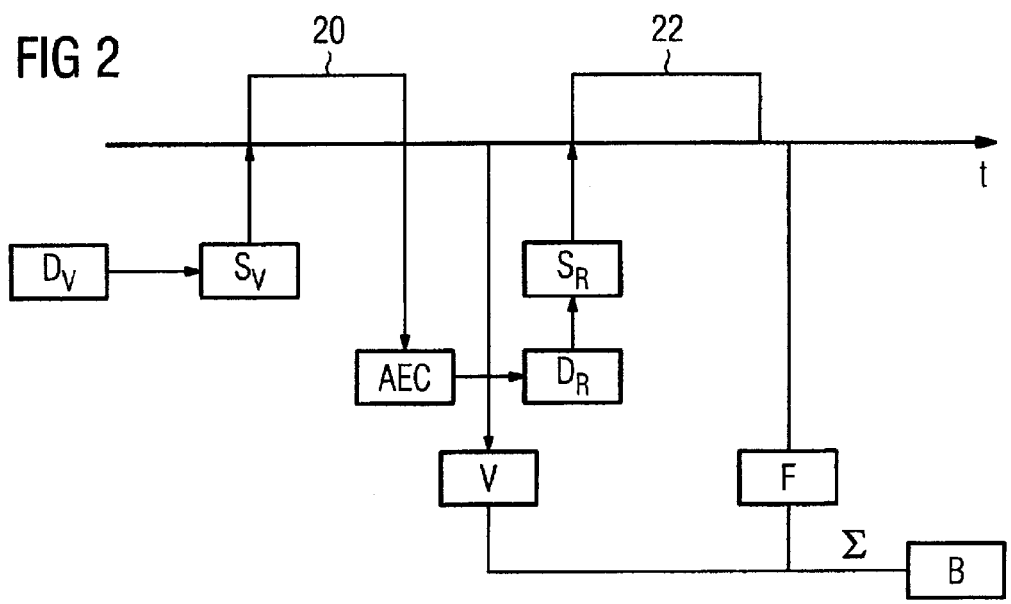

METHOD AND APPARATUS FOR GENERATION OF A DIGITAL X-RAY IMAGE OF AN EXAMINATION SUBJECT

BACKGROUND OF THE INVENTION

1. Field of the Invention

The invention concerns a method and an apparatus for generation of a digital x-ray image of an examination subject.

2. Description of the Prior Art

In the acquisition of an x-ray image of an examination subject, for example in mammography, it must be ensured that the acquisition parameters (in particular the applied dose) are correctly set in order to ensure an image quality suitable for diagnostic evaluation. In order to limit the radiation exposure of the irradiated region of the examination subject to the diagnostically-required minimum, it is sought to already correctly set the acquisition parameters in the first image acquisition. For this purpose, an arrangement known as an exposure automatic (AEC, automatic exposure control) is used.

In the generation of an analog x-ray image with an x-ray film, for example in analog mammography, a number of solid-state detectors are arranged behind the x-ray film (in the direction of propagation of the x-rays). These detectors measure the intensity of the x-rays transmitted through the x-ray film, and the output signals of which are used to control the acquisition parameters (for example exposure time, operating voltage of the x-ray tube, x-ray current, anode filter combination).

Due to the higher absorption of the x-ray detectors used in digital x-ray imaging, such an exposure control ensuing during the image acquisition is, however, not possible. In x-ray apparatuses with digital x-ray detectors the exposure control ensues by making an exposure known as a pre-shot with a low dose in a first step. The dose radiated in the pre-shot is so low that detector and quantum noise influence the measurement signal respectively acquired by the individual detectors to a significant degree. The signals of a number of individual detectors are therefore combined (binning, undersampling) into respective measurement values, such that only a few hundred measurement values have to be evaluated instead of multiple tens of thousands (orders of magnitude more). These measurement values are used for determination of the correct exposure time or total dose. The data acquired in the pre-shot, however cannot be used for the diagnostic x-ray image (i.e., an image of sufficient quality to allow a competent diagnosis to be made there from) due to the low dose, and thus represent a small but nevertheless undesirable additional dose exposure.

SUMMARY OF THE INVENTION

An object of the invention is to provide a method for generation of a digital x-ray image of an examination subject in which the disadvantages cited above are avoided. An object of the invention is to also provide an apparatus for implementation of such a method.

With regard to the method, the above object is achieved by determining using prior knowledge, a preliminary total dose required for correct exposure and a complete pre-image of the examination subject is acquired with a partial dose that is smaller than the preliminary total dose. A remaining dose is determined from the complete pre-image by evaluation thereof, and a complete following image is acquired with this remaining dose. The final x-ray image (used for diagnosis) is then assembled from the pre-image and the following image.

With this method it is ensured that the entire radiation exposure for the x-ray image can be utilized. Since a complete pre-image is acquired, meaning that a pre-image is generated having a spatial resolution corresponding to that of the final x-ray image, by the signals of all individual detectors being acquired separately from one another, this pre-image can be diagnostically utilized and can be assembled with the following image into an overall image.

The term "dose" as used herein is equivalent to the product of x-ray current and time (mAs), since the acquisition parameters that do not concern this current-time product but rather concern the other operating conditions of the x-ray tube are identical for pre-image and following image.

The image evaluation for determination of the remaining dose ensues with the methods as are known in the automatic exposure control (explained in the preceding) in digital x-ray diagnostics. There is a desired or target value of an image parameter for this exposure control, for example an average intensity or brightness value (pixel value) or a signal-to-noise ratio, in an image region (region of interest) evaluated for the exposure control. The required remaining dose then can be determined from the value of the image parameter measured in the pre-image and the desired value by means of a correlation between the dose and the value of the image parameter that is known from previous measurement and tabulation.

In order to minimize detector and quantum noise in the pre-image and in the following image, i.e. to ensure that the pre-image and the following image each can be diagnostically utilized, it is advantageous for the partial dose to be between 40% and 60% of the preliminary total dose. In other words, the first exposure ensues with a partial dose that does not in fact correspond to the actual necessary total dose or the predicted total dose, but is in the same order of magnitude and thus is significantly higher than the dose used in the pre-shot in the prior art for exposure control.

The prior knowledge necessary for the determination of the preliminary total dose encompasses experimental values (properties, for example tissue composition, bone ratio and thickness of the examination subject) stored, for example, in a look-up table for the respective application case. In mammography it has proven to be particularly simple and advantageous when a dose is selected as the preliminary total dose that is approximately 80 to 90% of the known (from the prior knowledge) average total dose of a 2 cm-thick compressed breast.

DESCRIPTION OF THE DRAWINGS

FIG. 1 shows an embodiment of an apparatus according to the invention in a schematic representation.

FIG. 2 is a flow chart of an embodiment of the inventive method.

DESCRIPTION OF THE PREFERRED EMBODIMENTS

As shown in FIG. 1, an apparatus for generation of a digital x-ray image B (in the shown example a mammography apparatus) has an x-ray tube 2 for generation of x-rays 3 that penetrate an examination subject 4. In the example the examination subject 4 is a female breast that is held between a compression plate 6 and a patient positioning table 8. The x-rays 4 penetrating the examination subject 4, the compression plate 6 and the patient positioning table 8 are acquired by a large-surface digital x-ray detector 10 that is composed of a number of individual detectors 12 arranged in a matrix-like array. A scattered-ray grid can be arranged in front of the x-ray detector 10 for suppression of scatter radiation.

The control of the x-ray tube 2 as well as of its operating parameters ensues by control signals S that are generated by a control and evaluation device 14. The acquisition parameters required for generation of a complete pre-image V can be set by the user using input and display elements, represented in the example as a keyboard 16 and a monitor 18. This pre-image V is acquired with a partial dose that is determined using a total dose determined by the user.

An automatic evaluation of the pre-image V acquired with the partial dose then ensues in the control and evaluation device 14 with the method as is known for automatic exposure control in order to determine the remaining dose required for generation of the x-ray image. Given otherwise unchanged acquisition parameters, a complete following image F is then acquired with this remaining dose. The complete pre-image V and the complete following image F are then combined into a final x-ray image B in the control and evaluation device 14. The actual total dose required for the final x-ray image B is the stored units of partial dose and remaining dose and normally does not coincide with the previously-predicted preliminary total dose.

The selection of the acquisition parameters and of the preliminary total dose for the pre-image V ensues by the personnel implementing the image acquisition using prior knowledge (for example look-up tables) in which are listed, for example, tissue composition, size and further subject parameters relating to the examination subject 4 as well as operating parameters of the x-ray tube 2 and the total dose normally required for these parameters or a first exposure time required for generation of the pre-image V. The preliminary total dose is a rough estimate. However, since the pre-image V is acquired with a significantly lower partial dose, namely approximately between 40% and 60% of this estimated or predicted preliminary total dose, an overexposure and an unnecessary dose exposure associated with this are precluded in practice.

In mammography, i.e. in the generation of an x-ray image B of the female breast, the partial dose can also be selected with the aid of tables in that approximately 80 to 90% of the known (from the prior knowledge) average total dose for the thinnest breast occurring in practice (i.e. for a compressed breast thickness of approximately 2 cm) is selected by default as the preliminary total dose. Given an average breast this then leads to a partial dose of approximately 50% of the second total dose, and given a breast with the highest compression thickness this then leads to a partial dose of approximately 10 to 20% of the second total dose.

In the flow chart of FIG. 2, a partial dose $D_V$ or partial exposure time is entered manually in a first step. The control signals $S_V$ associated with this partial dose $D_V$ are then generated in the control and evaluation device for the x-ray tube and a first exposure is conducted in a first time window 20. The measurement values acquired by the individual detectors are read out at the end of the time window 20 and assembled into the complete pre-image V as well as into a data set AEC that is suitable for the automatic exposure control. A calculation of the actual required, correct total dose or, respectively, the remaining dose $D_R$ or the remaining exposure time from this data set AEC ensues in a next step and the associated control signals $S_R$ for the x-ray tube are generated. A new exposure is subsequently conducted in a second time window 22. The individual detectors are read out and combined into a complete following image F, whereby the pre-image V and the following image F are subsequently added and assembled into the x-ray image B in this manner.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for generating a digital x-ray image of an examination subject, comprising the steps of:

determining a preliminary total x-ray radiation dose that is estimated, based on knowledge of the examination subject, to be necessary for obtaining a diagnostic image of an examination subject;

irradiating the examination subject with a partial dose of x-rays from an x-ray tube, that is less than said preliminary total dose, and detecting said x-rays attenuated by the examination subject with a digital x-ray detector to obtain a pre-image of the examination subject;

evaluating said pre-image to determine a remaining radiation dose, that has no fixed relation to said preliminary total dose, needed to produce the diagnostic image of the subject;

irradiating the examination subject with x-rays from said x-ray tube at said remaining radiation dose and detecting said x-rays attenuated by the examination subject with said digital x-ray detector to obtain a following image; and combining said pre-image and said following image to obtain a final x-ray image, as the diagnostic image of the subject.

2. A method as claimed in claim 1 comprising setting said partial dose in a range between 40% and 60% of said total dose.

3. A method as claimed in claim 1 wherein said examination subject is a female breast, and determining said total dose, as a default setting for said x-ray tube, as being between 80% and 90% of a known average total dose for a two cm-thick compressed female breast.

4. An apparatus for generating a digital x-ray image of an examination subject comprising:

an x-ray tube that emits x-ray radiation that irradiates an examination subject;

a digital x-ray detector that detects said x-ray radiation attenuated by the examination subject; and a control unit connected to said x-ray tube and to said digital x-ray a detector and having access to prior information about the examination subject, that determines a preliminary total x-ray radiation dose, using said prior information, that is an estimate of a dose necessary to obtain a diagnostic image of the examination subject, and that operates said x-ray tube at a partial dose, that is smaller than said preliminary total dose, to irradiate the examination subject with x-rays that are detected with said digital x-ray detector as a pre-image, and that evaluates said pre-image to determine a remaining x-ray radiation dose, having no fixed relation to said preliminary total dose, needed to produce the diagnostic image of the subject, and that operates said x-ray tube at said remaining dose to irradiate the examination subject with x-rays that are detected by said digital x-ray detector as a following image, and that combines said pre-image and said following image to obtain a final x-ray image, as the diagnostic image of the subject.

* * * * *